(12) United States Patent
Hiasa et al.

(10) Patent No.: US 8,277,793 B2
(45) Date of Patent: Oct. 2, 2012

(54) PROPHYLACTIC OR THERAPEUTIC AGENT FOR VIRAL DISEASE

(75) Inventors: Yoichi Hiasa, Ehime (JP); Hiroyuki Kuzuhara, Kanagawa (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 327 days.

(21) Appl. No.: 12/307,726

(22) PCT Filed: Jul. 6, 2007

(86) PCT No.: PCT/JP2007/063545
§ 371 (c)(1),
(2), (4) Date: Jul. 6, 2009

(87) PCT Pub. No.: WO2008/004653
PCT Pub. Date: Jan. 10, 2008

(65) Prior Publication Data
US 2009/0324541 A1 Dec. 31, 2009

(30) Foreign Application Priority Data
Jul. 7, 2006 (JP) ................................ 2006-187943

(51) Int. Cl.
*A61K 38/21* (2006.01)
*A61P 31/14* (2006.01)

(52) U.S. Cl. ..................................................... 424/85.4
(58) Field of Classification Search .................. 424/85.4
See application file for complete search history.

(56) References Cited

U.S. PATENT DOCUMENTS
6,306,862 B1  10/2001  Sasaki et al.

FOREIGN PATENT DOCUMENTS
| JP | 3279574 B2 | 2/2002 |
|---|---|---|
| RU | 2157215 C2 | 10/2000 |
| RU | 2182154 C2 | 5/2002 |
| WO | 9409793 A1 | 5/1994 |
| WO | 97/03088 A1 | 1/1997 |
| WO | 2005/097815 A1 | 10/2005 |

OTHER PUBLICATIONS

Cheney et al (Comparative Analysis of Anti-Hepatitis C Virus Activity and Gene Expression Mediated by Alpha, Beta and Gamma Interferons, Journal of Virology, Nov. 2002, pp. 11148-11154).*
Heathcote et al (Chronic Hepatitis C Virus Petients with Breakthroughs During Interferon Treatment Can Successfully Be Treated with Consensus Interferon, Hepatology, 1999, vol. 30, No. 2, pp. 562-566).*
The Japan Society of Hepatology, ed., "Mansei Kanen no chiryo gaido (Guidelines of treatment for chronic hepatitis)", Bunkodo Co., Ltd., 2006, p. 21, Translation.
Shiro Iino, "The guideline of treatment for hepatitis C", Nippon Rinsho, 2004, pp. 342-346, vol. 62, Suppl. 7, Translation.
Annual Review of Biochemistry, U.S.A., 1987, p. 727-777, vol. 56.
Shiro Iino, "Akkiraka ni natta interferon no kouka to genkai (Revealed effects and limit of interferon)", Naika, 1999, pp. 285-291, vol. 84, No. 2, Translation.
Thierry Poynard et al., "Randomised trial of Interferon *2b plus ribavirin for 48 weeks or for 24 weeks versus interferon *2b plus placebo for 48 weeks for treatment of chronic infection with hepatitis C virus", The Lancet, United Kingdom, Oct. 31, 1998, pp. 1426-1432, vol. 352, No. 9138.
Hepatology, U.S.A., Oct. 2005, vol. 42, p. 248A.
Hiasa Y. et al., "ME3738 effectively reduces HCV replication in a binary replication model", Hepatology, 2005, p. 248A, vol. 42, No. 4.
Japan Pharmaceutical Information Center, Iryoyaku Nippon Iyakuhinshu, Jiho Inc., Oct. 25, 2004, the paragraph of "Adaptation" on pp. 319 to 320.
Hiromitsu Kumada, "Virus-sei Kan'en no Genkyo to Tenbo", Ishiyaku Pub., Inc., Jul. 25, 2003, pp. 76 to 80.
Office Action issued Feb. 2, 2011 in Russian Patent Application No. 2009104066/14 (in the name of Meiji Seika Kaisha, Ltd., JP).
Mashkovsky M.D., Drugs, M., "Medicine", 2001, 2: 322-324.

* cited by examiner

*Primary Examiner* — San-ming Hui
*Assistant Examiner* — Kathrien Cruz
(74) *Attorney, Agent, or Firm* — Sughrue Mion, PLLC

(57) ABSTRACT

A prophylactic or therapeutic agent for a viral disease, characterized by combining 22β-methoxyolean-12-ene-3β,24(4β)-diol with an interferon as active ingredients is disclosed. The prophylactic or therapeutic agent of the present invention exhibits a high therapeutic effect by administering 22β-methoxyolean-12-ene-3β,24(4β)-diol and interferon as a combination thereof.

6 Claims, 2 Drawing Sheets

1: Control
2: 22β-methoxyolean-12-ene-3β,24(4β)-diol (0.1 μmol/L)
3: IFN (100 IU/mL)
4: 22β-methoxyolean-12-ene-3β,24(4β)-diol (0.1 μmol/L) and IFN (100 IU/mL)

1: Control
2: 22β-methoxyolean-12-ene-3β,24(4β)-diol (0.1 μmol/L)
3: IFN (100 IU/mL)
4: 22β-methoxyolean-12-ene-3β,24(4β)-diol (0.1 μmol/L) and IFN (100 IU/mL)

PROPHYLACTIC OR THERAPEUTIC AGENT FOR VIRAL DISEASE

CROSS REFERENCE TO RELATED APPLICATIONS

This application is a National Stage of International Application No. PCT/JP2007/063545 filed Jul. 6, 2007, claiming priority based on Japanese Patent Application No. 2006-187943 filed Jul. 7, 2006, the contents of all of which are incorporated herein by reference in their entirety.

TECHNICAL FIELD

The present invention relates to a prophylactic or therapeutic agent for a viral disease, characterized by combining 22β-methoxyolean-12-ene-3β,24(4β)-diol with an interferon.

BACKGROUND ART

In Japan, an estimated 1.5-2.0 million people are persistently infected with hepatitis C virus (HCV), and it is assumed that most carriers show the symptoms of chronic hepatitis (see non-patent reference 1). With respect to hepatitis B, there are many cases where the infection does not cause chronic hepatitis, but directly develops liver cancer. By contrast, 80 to 90% of HCV-infected persons develop chronic liver disease based on observations of liver tissue, and there is a possibility that 50 to 60% of HCV-infected persons develop cirrhosis or hepatocellular carcinoma via chronic hepatitis (see non-patent reference 2). HCV infection has become a major clinical problem worldwide.

Interferons (IFNs) are a highly-homologous and species-specific protein family that regulates the immune response by inhibiting viral replication and cell proliferation, and it is known that there are four classes of interferons in humans (non-patent reference 3).

Interferons are applied to various viral diseases on the basis of the antiviral effects thereof. In particular, for the treatment of chronic hepatitis C that is caused by the infection of HCV, a virus having a positive-stranded RNA genome, IFNs are widely used to eliminate HCV. However, it is known that IFNs have low therapeutic effects for patients infected with HCV genotype 1b or having a high viral load (1 Meq or higher) (see non-patent references 4 and 5). This genotype and high viral load are factors that affect the therapeutic effects of IFN, and such patients account for 70% or more of those with chronic hepatitis C in Japan. In addition, side effects such as fever, weakness, and psychiatric disorders are frequently observed.

As conventional treatments for a patient infected with genotype 1b and having a high viral load, a combination therapy of ribavirin with IFN, and a combination therapy of ribavirin with PEG-interferon α-2a (PEG-IFN α-2a) or PEG-interferon α-2b (PEG-IFN α-2b) are known. These therapeutic effects (complete response rate) are not enough. Even the most effective combination therapy of ribavirin with PEG-IFN at present shows a complete response rate of, at most, approximately 50%. Further, compared to a treatment with IFN alone, side effects such as reductions of hemoglobin, erythrocytes, and leukocytes are frequently observed in the IFN/ribavirin therapy. When PEG-IFN α-2a is used, influenza-like symptoms are milder than those caused by IFN, but skin reactions and reductions of lymphocytes, platelets, and erythrocytes are more frequently observed. In the combination therapy of ribavirin with PEG-IFN α-2b, disorders at the injection site frequently occur, recovery of laboratory test values for adverse effects on hematology slows slightly and, in elderly patients, the frequencies of highly abnormal laboratory test values and dose reduction tend to become high. Under these circumstances, the development of treatments effective for a case where sufficient effects are not obtained by IFN treatment, a case where effectiveness by IFN administration is not expected due to genotype 1b or a high viral load, a case of an elderly patient, a case where the infection develops cirrhosis, and the like, is desired.

22β-methoxyolean-12-ene-3β,24(4β)-diol is a compound having the following structure, and is known to have an inhibitory effect on hepatocyte disorder (see patent references 1 and 2).

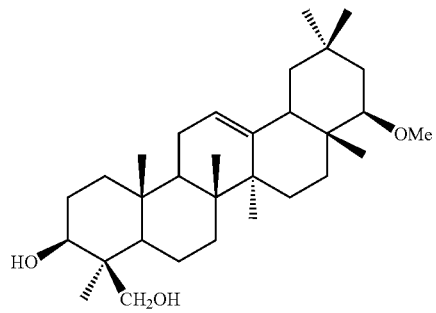

Further, it was reported that 22β-methoxyolean-12-ene-3β,24(4β)-diol had an anti-HCV effect (see non-patent reference 6), and this compound is expected to be developed as a therapeutic agent for viral liver diseases. However, effects obtained by combining this compound with other drugs have not been studied.

[patent reference 1] International Publication WO97/03088
[patent reference 2] Japanese Patent No. 3279574
[non-patent reference 1] The Japan Society of Hepatology, ed., "Mansei kanen no chiryo gaido (Guidelines of treatment for chronic hepatitis)", BUNKODO Co., Ltd., 2006, p. 21
[non-patent reference 2] Shiro IINO, "The guideline of treatment for hepatitis C", Nippon Rinsho, 2004, vol. 62, suppl. 7, p. 342-346
[non-patent reference 3] Annual Review of Biochemistry, U.S.A., 1987, vol. 56, p. 727-777
[non-patent reference 4] Shiro IINO, "Akiraka ni natta interferon no kouka to genkai (Revealed effects and limit of interferon)", Naika, 1999, vol. 84, no. 2, p. 285-291
[non-patent reference 5] Lancet, United Kingdom, 1998, vol. 352, no. 9138, p. 1426-1432
[non-patent reference 6] Hepatology, U.S.A., 2005, vol. 42, p. 248A

DISCLOSURE OF THE INVENTION

Problems to be Solved by the Invention

To solve the above problems, the present inventors have conducted intensive studies of agents effective for preventing or treating viral diseases, particularly infectious diseases due to a virus having a positive-stranded RNA genome, and, as a result, found that a combination of 22β-methoxyolean-12-ene-3β,24(4β)-diol with interferon enhanced an inhibitory effect on HCV replication, and might be a useful drug for preventing or treating the viral diseases, and completed the present invention.

Means for Solving the Problems

The present invention relates to

[1] a prophylactic or therapeutic agent for a viral disease, characterized by combining 22β-methoxyolean-12-ene-3β,24(4β)-diol with an interferon as active ingredients;
[2] the prophylactic or therapeutic agent of [1], wherein the viral disease is caused by an RNA virus;
[3] the prophylactic or therapeutic agent of [2], wherein the RNA virus has a positive-stranded RNA genome;
[4] the prophylactic or therapeutic agent of [3], wherein the RNA virus is hepatitis C virus;
[5] the prophylactic or therapeutic agent of [1], wherein the viral disease is hepatitis C, or cirrhosis or hepatocellular carcinoma caused by hepatitis C.
[6] a method of preventing or treating a viral disease, comprising administering to a subject in need thereof 22β-methoxyolean-12-ene-3β,24(4β)-diol and interferon in an amount effective therefor;
[7] the method of [6], wherein the viral disease is caused by an RNA virus;
[8] the method of [7], wherein the RNA virus has a positive-stranded RNA genome;
[9] the method of [8], wherein the RNA virus is hepatitis C virus;
[10] the method of [6], wherein the viral disease is hepatitis C, or cirrhosis or hepatocellular carcinoma caused by hepatitis C;
[11] a use of 22β-methoxyolean-12-ene-3β,24(4β)-diol and interferon in the manufacture of a prophylactic or therapeutic agent for a viral disease;
[12] the use of [11], wherein the viral disease is caused by an RNA virus;
[13] the use of [12], wherein the RNA virus has a positive-stranded RNA genome;
[14] the use of [13], wherein the RNA virus is hepatitis C virus; and
[15] the use of [11], wherein the viral disease is hepatitis C, or cirrhosis or hepatocellular carcinoma caused by hepatitis C.

Effects of the Invention

The prophylactic or therapeutic agent of the present invention exhibits high prophylactic or therapeutic effects on viral diseases, preferably viral diseases caused by an RNA virus, more preferably viral diseases caused by a virus having a positive-stranded RNA genome, most preferably hepatitis C caused by hepatitis C virus, or cirrhosis or hepatocellular carcinoma caused by hepatitis C, by administering 22β-methoxyolean-12-ene-3β,24(4β)-diol and interferon in combination thereof.

BEST MODE FOR CARRYING OUT THE INVENTION

Figure 1:
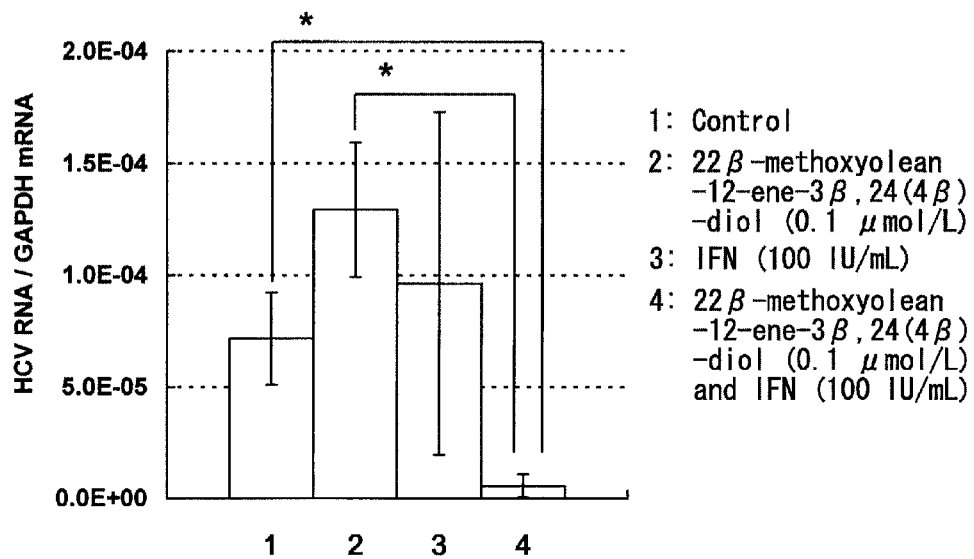
FIG. 1 is a graph showing inhibitory effects of 22β-methoxyolean-12-ene-3β,24(4β)-diol alone, IFN alone, and a combination of 22β-methoxyolean-12-ene-3β,24(4β)-diol with IFN, on HCV replication at day 1 after Ad-T7pol infection.

The term "viral diseases" means diseases caused by a virus. Viruses which cause the diseases include DNA viruses and RNA viruses. DNA viruses may be exemplified by hepatitis B virus, poxvirus, herpes virus, adenovirus, and parvovirus. RNA viruses may be exemplified by reovirus, togavirus, coronavirus, rhabdovirus, paramyxovirus, orthomyxovirus, bunyavirus, arenavirus, retrovirus, picornavirus, and calicivirus.

As the viruses in the prophylactic or therapeutic agent of the present invention, RNA viruses are preferable, RNA viruses having a positive-stranded RNA genome are more preferable, and hepatitis C virus is most preferable. RNA viruses having a positive-stranded RNA genome may be exemplified by poliovirus, coxsackievirus, echovirus, enterovirus, rhinovirus, hepatitis A virus, hepatitis E virus, rubella virus, Eastern equine encephalitis virus, Western equine encephalitis virus, yellow fever virus, dengue fever virus, St. Louis encephalitis virus, Hepatitis C virus, hepatitis G virus, coronavirus, West Nile virus, and vesicular stomatitis virus.

The RNA viruses having a positive-stranded RNA genome replicate in a common fashion. That is, cells are infected with a virus, and the viral RNA enters the cells. The entered viral RNA is directly translated to viral proteins, such as RNA-dependent RNA polymerase necessary to replicate viral RNA. These translated proteins replicate viral RNA by using the entered viral RNA as a template. The replicated viral RNA is incorporated into self-produced proteins, and the resulting viruses are released to the outside of the cells (see JP 2005-35913 A).

An anti-viral action mechanism of interferon is proposed in, for example, JP 2005-35913 A, as follows: interferon binds to a receptor on the surface of a cell, and then, a protein having anti-viral effects is induced in the cell. For example, oligo-2'-5'-adenylate is generated by the action of 2'-5'-adenylate synthetase induced by interferon. It is considered that oligo-2'-5'-adenylate activates RNA-dependent RNAase, the activated RNA-dependent RNAase degrades the viral RNA, and as a result, interferon exhibits anti-viral effects. According to the above action mechanism, it is considered that the prophylactic or therapeutic agent of the present invention is effective for RNA viruses having a positive-stranded RNA genome.

In the viral diseases, examples of diseases caused by hepatitis viruses [such as hepatitis B virus (HBV) and hepatitis C virus (HCV)] include liver disorders and the like of acute or chronic viral hepatitis (such as hepatitis B and hepatitis C), preferably hepatitis C, or cirrhosis or hepatocellular carcinoma caused by hepatitis C. Hepatitis B is defined as hepatitis caused by HBV infection, and Hepatitis C is defined as hepatitis caused by HCV infection. Chronic hepatitis is defined as a clinical condition where inflammation in the liver persists, or appears to persist, for 6 months or more. Liver disorders are defined as inflammatory diseases in the liver, and may be used as a concept including fatty liver, cirrhosis, and hepatocellular carcinoma according to the progression of symptoms.

22β-Methoxyolean-12-ene-3β,24(4β)-diol, which may be used as one of the active ingredients for the prophylactic or therapeutic agent of the present invention, is a known compound, and can be obtained by, for example, the method described in Example 22 (Compound 27) of WO97/03088.

In general, 22β-methoxyolean-12-ene-3β,24(4β)-diol may be orally administered as a conventional pharmaceutical formulation, such as capsules, microcapsules, tablets, granules, fine granules, powders, and the like. Further, it may be parenterally administered (for example, intravenous injection, intramuscular injection, subcutaneous administration, intraperitoneal administration, rectal administration, percutaneous administration) as a conventional pharmaceutical formulation, such as injections (intravenous, intramuscular, and the like) and the like. These formulations can be prepared by a conventional method using an excipient, a filler, a binder, a wetting agent, a disintegrating agent, a surfactant, a lubricant, a dispersing agent, a buffer, a preservative, a solubilizer, an antiseptic, a flavor, a soothing agent, a stabilizer, and the like. Examples of the above additives which are nontoxic and suitable for the preparations include lactose, fructose, glucose, starch, gelatin, magnesium carbonate, synthetic magnesium silicate, talc, magnesium stearate, methylcellulose, carboxymethylcellulose or a salt thereof, gum arabic, polyethylene glycol, syrup, vaseline, glycerin, ethanol, propylene glycol, citric acid, sodium chloride, sodium sulfite, sodium phosphate, and the like.

In the prophylactic or therapeutic agent of the present invention, the form, the route of administration, the dose, the period of administration, and the like of 22β-methoxyolean-12-ene-3β,24(4β)-diol may be appropriately selected in accordance with, for example, the weight, the age, the symptoms, and the like of a patient. Further, these are not particularly limited, so long as the antiviral effect of 22β-methoxyolean-12-ene-3β,24(4β)-diol is enhanced when combined with interferon. For example, a daily dose of 1 to 1000 mg is orally or parenterally administered as a single dose or plural divided doses. Preferably, a daily dose of 25 to 800 mg is divided into two doses, which are orally or parenterally administered.

An interferon (IFN), which may be used as the other active ingredient for the prophylactic or therapeutic agent of the present invention, is not limited. Commercially available IFNs or IFNs under clinical development include, for example, natural IFNα (Sumiferon: Dainippon Sumitomo Pharma Co., Ltd.), IFNα-2a, IFNα-2b (Intron A: Schering-Plough), polyethylene glycol (PEG)-natural IFNα, PEG-IFNα-2a (Pegasys: Chugai Pharmaceutical Co., Ltd.), PEG-IFNα-2b (PEG-Intron A), natural IFNβ (IFNβ Mochida: Mochida Pharmaceutical Co., Ltd., and Feron: Toray Industries, Inc.), PEG-natural IFNβ, natural IFNγ, consensus IFN (Advaferon: Astellas Pharma Inc.), PEG-consensus IFN, combinations thereof, and the like.

In the prophylactic or therapeutic agent of the present invention, the dose, duration, schedule, route, and the like for the administration of IFN are not particularly limited, so long as it is effective in the prevention or treatment of the viral diseases. For example, with respect to hepatitis C, a daily dose of 100,000 to 10,000,000 I.U. is subcutaneously, intramuscularly, or intravenously administered as a single dose or plural divided doses continuously or intermittently (such as three times per week) for 2 to 48 weeks, in general, but this administration can be appropriately modified in accordance with the type or amount of a virus, the weight or age of a patient, and the like. Preferably, a daily dose of 6,000,000 to 10,000,000 I.U. is administered continuously for 2 to 8 weeks followed by intermittent administration for 22 to 46 weeks, but this schedule can be appropriately modified in accordance with the type or form of IFN to be used.

The combination ratio (usage ratio or composition ratio) of 22β-methoxyolean-12-ene-3β,24(4β)-diol and interferon is not particularly limited, so long as it is effective in the prevention or treatment of the viral diseases. For example, with respect to hepatitis C, the combination ratio can be appropriately selected from 1 mg:100,000 I.U. to 1000 mg:10,000,000 I.U., preferably 25 mg:1,000,000 I.U. to 800 mg:10,000,000 I.U., as a daily dose.

In the prophylactic or therapeutic agent of the present invention, 22β-methoxyolean-12-ene-3β,24(4β)-diol and interferon are administered in combination. The term "administration in combination" includes an embodiment in which a single preparation of 22β-methoxyolean-12-ene-3β,24(4β)-diol and another single preparation of interferon are administered simultaneously or with an interval. In this embodiment, the number of administrations of one preparation may be the same as, or different from that of another preparation.

Appropriate doses and intervals of 22β-methoxyolean-12-ene-3β,24(4β)-diol and interferon can be selected in accordance with a controlled clinical trial.

The prophylactic or therapeutic agent of the present invention may be one dosage form comprising the two active ingredients in a composition, or two dosage forms separately comprising the two active ingredients in different compositions.

EXAMPLES

The present invention now will be further illustrated by, but is by no means limited to, the following Example.

Example 1

Confirmation of Inhibitory Effect of Combination of 22β-methoxyolean-12-ene-3β,24(4β)-diol and Interferon on HCV Replication In this example, a full-genome HCV replication model as described in non-patent reference 6 was used to evaluate the prophylactic or therapeutic agent of the present invention.

A cDNA was obtained from a full-length clone of infectious hepatitis C virus (HCV) H77 [GenBank AF011751; Yanagi, M., Purcell, R. H., Emerson, S. U., Bukh, J. Proc. Natl. Acad. Sci. U.S.A. 94(16), 8738-8743(1997)] of genotype 1a which was refractory to treatment with interferon, and was adapted to prepare a plasmid (pT7-flHCV-Rz) containing the cDNA with a T7 promoter and a hepatitis delta virus ribozyme gene at the 5' and 3' termini thereof, respectively. HepG2 cells (resource number: JCRB1054) inoculated on 6-well plates were transfected with plasmid pT7-flHCV-Rz (3 μg/well). After 24 hours from the transfection, the HepG2 cells were infected with a recombinant adenovirus expressing T7 polymerase (Ad-T7pol) (10 PFU/cell) to express the HCV gene in the host cells. In this replication model, RNA completely homologous to the HCV gene (positive strand) is transcribed in the cells. This HCV positive strand is translated to a NS5B protein having an RNA-dependent RNA polymerase activity. As a result, an HCV negative strand is transcribed, and the intracellular replication of HCV is observed.

After 3 hours from the Ad-T7pol infection, 22β-methoxyolean-12-ene-3β,24(4β)-diol and/or IFN-α 2b (Intron A:

Schering-Plough) were added to the cells, alone or in combination, to examine inhibitory effects thereof on HCV replication. 22β-methoxyolean-12-ene-3β,24(4β)-diol and IFN-α 2b were added to each culture medium (2 mL) at final concentrations of 0.1 μmol/L and 100 IU/mL, respectively. Culture media were exchanged after 1 day from the Ad-T7pol infection, for new culture liquids containing the above test compound(s) at the same concentration(s). As a control, dimethyl sulfoxide (DMSO), which was used as a solvent for 22β-methoxyolean-12-ene-3β,24(4β)-diol, was added alone to the culture medium at a final concentration of 0.1%. This experiment was carried out under conditions where the cytotoxicity of each test compound was not observed.

Cells were collected at day 1, day 2, and day 3 after the Ad-T7pol infection, and RNAs were extracted from the cells. The expression of HCV RNA was quantified by performing reverse-transcription using rTth DNA polymerase followed by real-time PCR (Light Cycler: Roche Diagnostics). The expression of mRNA of glyceraldehyde-3-phosphate dehydrogenase (GAPDH), which was a housekeeping gene of the host cell, was quantified by performing reverse-transcription using MuLV reverse-transcriptase followed by real-time PCR. As primers for real-time PCR, Sense Primer:

5'-GCA GAA AGC GTC TAG CCA TGG CGT-3' (SEQ ID NO.: 1, 68-91 nt of 5'UTR), and

Antisense Primer:

5'-CTC GCA AGC ACC CTA TCA GGC AGT-3' (SEQ ID NO.: 2, 311-288 nt of 5'UTR)

were used for HCV RNA, and a commercially available kit (Human GAPDH primer set: Search LC) was used for GAPDH.

Figure 2:
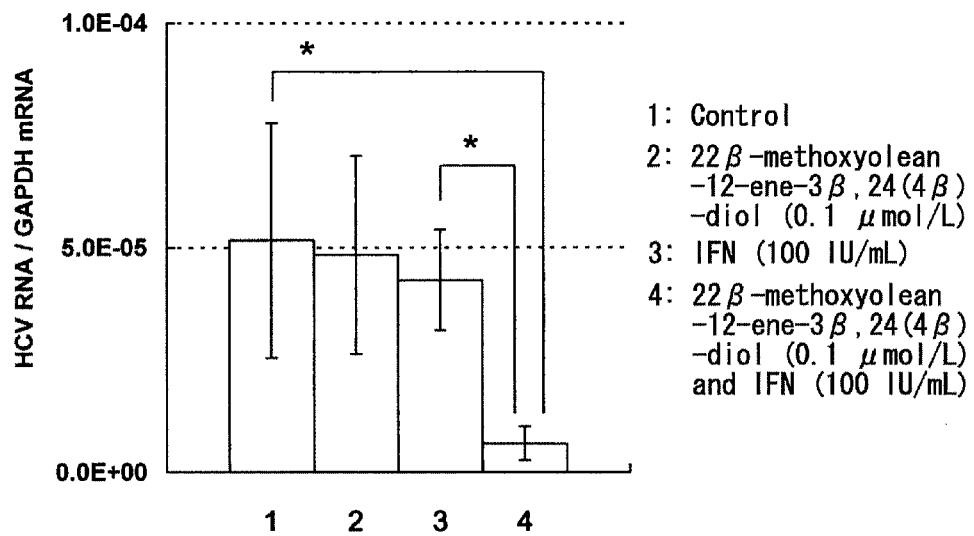
FIG. 2 is a graph showing inhibitory effects of 22β-methoxyolean-12-ene-3β,24(4β)-diol alone, IFN alone, and a combination of 22β-methoxyolean-12-ene-3β,24(4β)-diol with IFN, on HCV replication at day 2 after Ad-T7pol infection.
Figure 3:
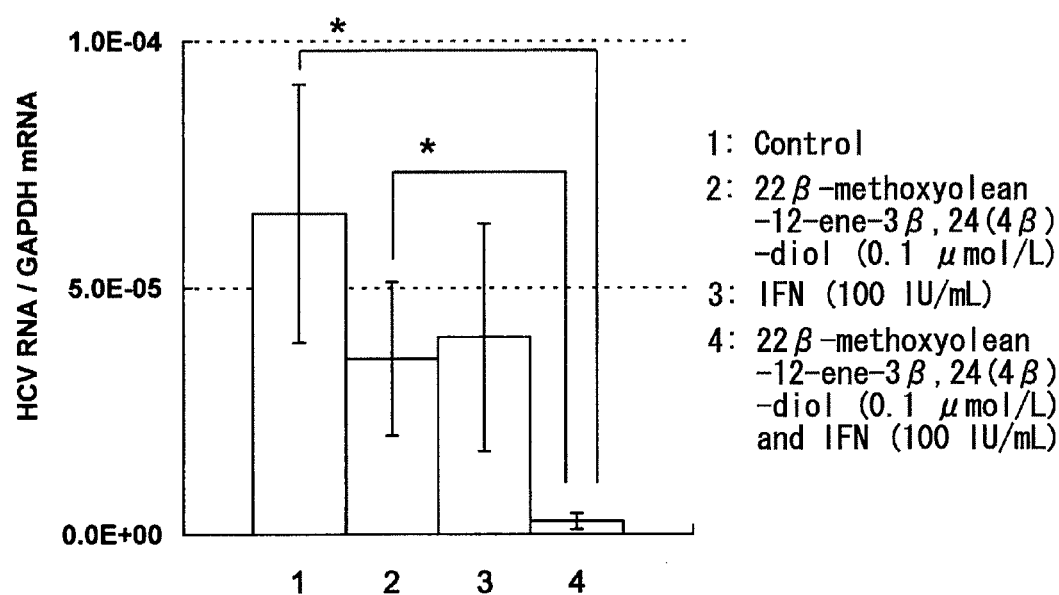
FIG. 3 is a graph showing inhibitory effects of 22β-methoxyolean-12-ene-3β,24(4β)-diol alone, IFN alone, and a combination of 22β-methoxyolean-12-ene-3β,24(4β)-diol with IFN, on HCV replication at day 3 after Ad-T7pol infection.

The results are shown in FIGS. 1 to 3. In FIGS. 1 to 3, lane 1 is the result of the control, lane 2 is the result of 22β-methoxyolean-12-ene-3β,24(4β)-diol (0.1 μmol/L) alone, lane 3 is the result of IFN (100 IU/mL) alone, and lane 4 is the result of 22β-methoxyolean-12-ene-3β,24(4β)-diol and IFN in combination.

As a result, it was confirmed that the inhibitory effect on HCV replication was synergistically enhanced when 22β-methoxyolean-12-ene-3β,24(4β)-diol was combined with IFN, significantly, compared to single administration of each compound.

INDUSTRIAL APPLICABILITY

According to the present invention, a prophylactic or therapeutic agent for a viral disease (preferably an agent effective for infection with a virus having a positive-stranded RNA genome, more preferably an agent effective for hepatitis C caused by hepatitis C virus, or cirrhosis or hepatocellular carcinoma caused by hepatitis C), characterized by combining 22β-methoxyolean-12-ene-3β,24(4β)-diol with an interferon, can be provided.

Although the present invention has been described with reference to specific embodiments, various changes and modifications obvious to those skilled in the art are possible without departing from the scope of the appended claims.

The invention claimed is:

1. A pharmaceutical composition, comprising 22β-methoxyolean-12-ene-3β,24(4β)-diol and an interferon α.

2. The pharmaceutical composition according to claim 1, wherein the interferon α is at least one IFNα selected from the group consisting of natural IFNα, IFNα-2a, IFNα-2b, PEG-natural IFNα, PEG-IFNα-2a and PEG-IFNα-2b.

3. The pharmaceutical composition according to claim 1, wherein the composition is a single preparation comprising the combination of 22β-methoxyolean-12-ene-3β,24(4β)-diol and the interferon α.

4. The pharmaceutical composition according to claim 1, wherein the composition is a combination of a first single preparation comprising the 22β-methoxyolean-12-ene-3β,24 (4β)-diol and a second single preparation comprising the interferon α.

5. The pharmaceutical composition according to claim 3, wherein the 22β-methoxyolean-12-ene-3β,24(4β)-diol and the interferon α are in a combination ratio from 1 mg:100,000 I.U. to 1000 mg:10,000,000 I.U.

6. The pharmaceutical composition according to claim 5, wherein the 22β-methoxyolean-12-ene-3β,24(4β)-diol and the interferon α are in a combination ratio from 25 mg:1,000, 000 I.U. to 800 mg:10,000,000 I.U.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Hepatitis C virus

<400> SEQUENCE: 1
gcagaaagcg tctagccatg gcgt                                           24

<210> SEQ ID NO 2
<211> LENGTH: 24
<212> TYPE: DNA
<213> ORGANISM: Hepatitis C virus

<400> SEQUENCE: 2
ctcgcaagca ccctatcagg cagt                                           24
```